(12) United States Patent
Hayakawa

(10) Patent No.: US 11,672,406 B2
(45) Date of Patent: Jun. 13, 2023

(54) ENDOSCOPE, DISTAL END COVER, AND ENDOSCOPE SYSTEM

(71) Applicant: OLYMPUS CORPORATION, Tokyo (JP)

(72) Inventor: Fumitoshi Hayakawa, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 260 days.

(21) Appl. No.: 16/893,858

(22) Filed: Jun. 5, 2020

(65) Prior Publication Data

US 2020/0352419 A1    Nov. 12, 2020

Related U.S. Application Data

(63) Continuation of application No. PCT/JP2018/030799, filed on Aug. 21, 2018.

(30) Foreign Application Priority Data

Dec. 12, 2017  (JP) .............................. JP2017-237898

(51) Int. Cl.
*A61B 1/00* (2006.01)
*A61B 1/005* (2006.01)

(52) U.S. Cl.
CPC .......... *A61B 1/00098* (2013.01); *A61B 1/005* (2013.01); *A61B 1/00137* (2013.01)

(58) Field of Classification Search
CPC . A61B 1/00098; A61B 1/018; A61B 1/00137; A61B 1/00101; A61B 1/0008; A61B 1/00089; A61B 1/005
See application file for complete search history.

(56) References Cited

U.S. PATENT DOCUMENTS 5,860,913 A    1/1999  Yamaya et al.
2007/0246506 A1  10/2007  Hamazaki et al.
(Continued)

FOREIGN PATENT DOCUMENTS

EP    1 849 397 A    10/2007
JP    H09-299316 A    11/1997
(Continued)

OTHER PUBLICATIONS

International Search Report dated Oct. 23, 2018 issued in International Application No. PCT/JP2018/030799.

*Primary Examiner* — Aaron B Fairchild
(74) *Attorney, Agent, or Firm* — Scully, Scott, Murphy & Presser, P.C.

(57) ABSTRACT

An endoscope system includes: an endoscope including an insertion section, a distal end member disposed on a distal end portion of the insertion section, and a ring-shaped insulation member disposed on a proximal end side of the distal end member and a distal end cover including an opening that allows exposure of a portion of the distal end member and an inner peripheral surface disposed on a proximal end side with respect to the opening and in close contact with an outer peripheral surface of the insulation member. The outer peripheral surface of the insulation member and the inner peripheral surface of the distal end cover in close contact with the outer peripheral surface are formed in a shape formed by connecting a plurality of curved surfaces having different curvatures about the axis over an entire circumference about the axis.

10 Claims, 4 Drawing Sheets

(56) References Cited

U.S. PATENT DOCUMENTS

2017/0000317 A1\* 1/2017 Iizuka .................. A61B 1/0615
2019/0059702 A1\* 2/2019 Hosogoe ............ A61B 1/00101

FOREIGN PATENT DOCUMENTS

| JP | H10-155732 A | 6/1998 | | |
|---|---|---|---|---|
| JP | 2002-204774 A | 7/2002 | | |
| JP | 2004-298244 A | 10/2004 | | |
| JP | 2007-289434 A | 11/2007 | | |
| WO | 2016/021234 A1 | 2/2016 | | |
| WO | WO-2016021234 A1 \* | 2/2016 | ............... | A61B 1/00 |

\* cited by examiner

ENDOSCOPE, DISTAL END COVER, AND ENDOSCOPE SYSTEM

CROSS REFERENCE TO RELATED APPLICATION

This application is a continuation application of PCT/JP2018/030799 filed on Aug. 21, 2018 and claims benefit of Japanese Application No. 2017-237898 filed in Japan on Dec. 12, 2017, the entire contents of which are incorporated herein by this reference.

BACKGROUND OF THE INVENTION

1. Field of the Invention

The present invention relates to an endoscope, a distal end cover mounted on a distal end portion of an insertion section of the endoscope, and an endoscope system which includes the endoscope and the distal end cover.

2. Description of the Related Art

For example, as described in International Publication No. 2016/021234, there has been known a medical endoscope of a type where a cover is mounted on a distal end portion of an insertion section. In performing high frequency cauterization by an electric surgical knife or the like using an endoscope inserted into a subject, to prevent leaking of a high frequency current, the cover is made of a resin having an electrical insulation property. The cover has an inner peripheral surface which is brought into close contact with an outer periphery of the distal end portion.

In International Publication No. 2016/021234, there has been disclosed a technique where a to-be-tom-apart portion which is torn apart when a user applies force to the to-be-torn-apart portion is formed on a cover so that the cover can be easily removed from a distal end portion and a reuse of the cover is prevented.

SUMMARY OF THE INVENTION

According to an aspect of the present invention, there is provided an endoscope system which includes: an endoscope including an insertion section extending in a predetermined axis direction, a distal end member disposed on a distal end portion of the insertion section, and a ring-shaped insulation member disposed on a proximal end side of the distal end member and about the axis; and a distal end cover mounted on the distal end portion of the insertion section, the distal end cover including an opening that allows exposure of a portion of the distal end member and an inner peripheral surface disposed on a proximal end side with respect to the opening and being brought into close contact with an outer peripheral surface of the insulation member, wherein the outer peripheral surface of the insulation member and the inner peripheral surface of the distal end cover which is brought into close contact with the outer peripheral surface are formed in a shape which is formed by connecting a plurality of curved surfaces having different curvatures about the axis over an entire circumference about the axis.

According to an aspect of the present invention, there is provided a distal end cover which is disposed on an endoscope and mounted on a distal end portion of an insertion section extending along a predetermined axis, the distal end cover includes: an opening that allows exposure of a portion of the distal end portion; and an annular portion disposed on a proximal end side of the insertion section with respect to the opening, the annular portion including an inner peripheral surface which is brought into close contact with an outer peripheral surface of the distal end portion, the inner peripheral surface being formed in a shape which is formed by connecting a plurality of curved surfaces having different curvatures about the axis over an entire circumference.

According to an aspect of the present invention, there is provided an endoscope which includes: a distal end member being disposed on a distal end of an insertion section which extends along a predetermined axis, wherein a cover is mounted on the distal end member; and a ring-shaped insulation member disposed on a proximal end side of the distal end member and about the axis, wherein an outer peripheral surface of the insulation member is brought into close contact with an inner peripheral surface of the cover, the outer peripheral surface being formed in a shape which is formed by connecting a plurality of curved surfaces having different curvatures about the axis over an entire circumference.

DETAILED DESCRIPTION OF THE PREFERRED EMBODIMENT

Figure 1:
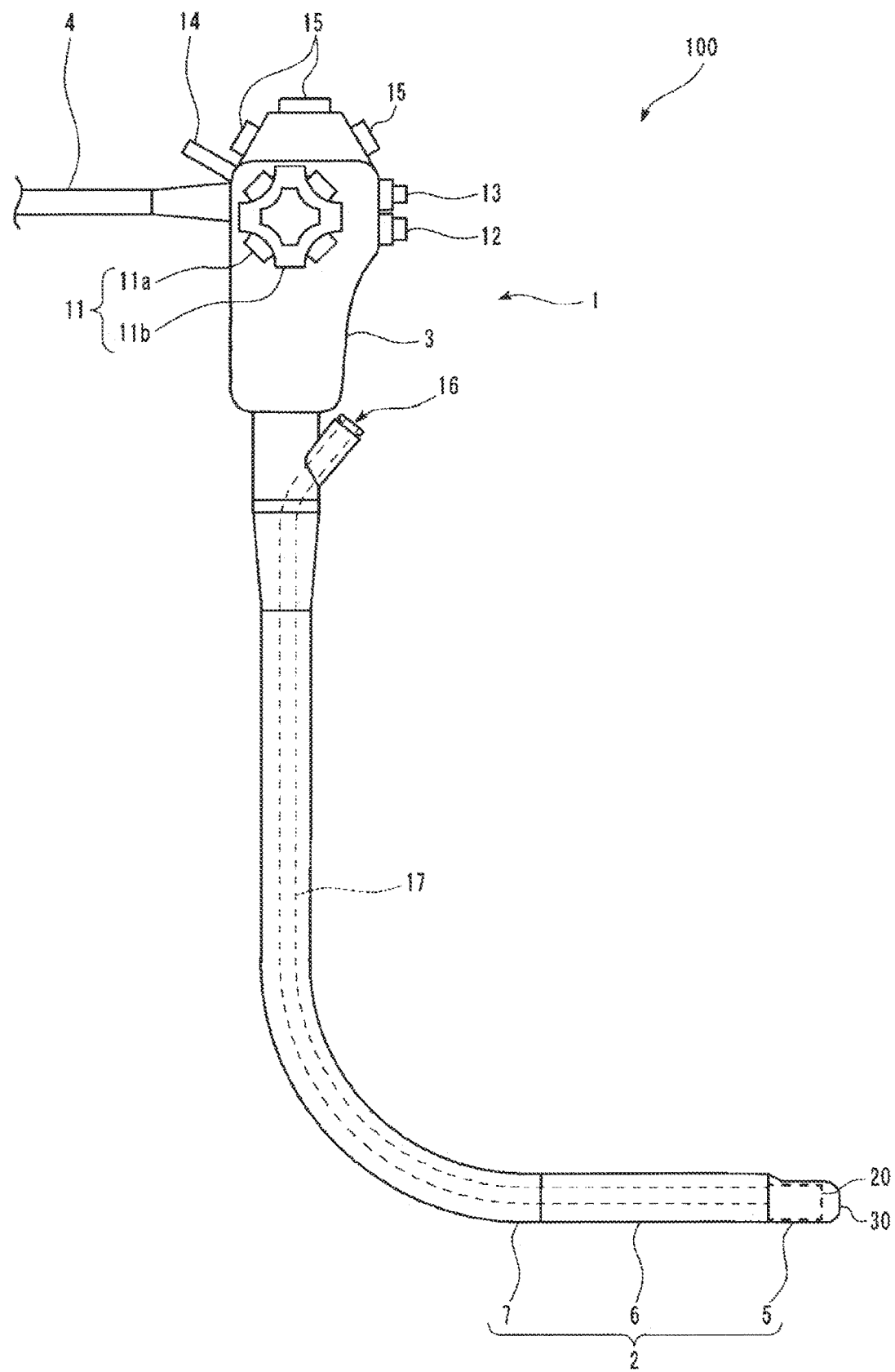
FIG. 1 is a view showing a schematic configuration of an endoscope system.

Hereinafter, a preferred embodiment of the present invention is described with reference to drawings. In the respective drawings used in the description made hereinafter, to set sizes of respective constitutional components to a level that the respective constitutional components are recognizable on the drawings, magnifications are made different for the respective constitutional components. The present invention is not limited only to the number of constitutional components, shapes of the constitutional components, ratios between sizes of the respective constitutional components, and the relative positional relationships of the respective constitutional components shown in the drawings.

FIG. 1 is a view showing a schematic configuration of an endoscope system 100. The endoscope system 100 according to the embodiment includes an endoscope 1 and a distal end cover 30. As an example of the embodiment, the endoscope 1 is a side-viewing endoscope.

The endoscope 1 includes: an insertion section 2 inserted into a subject; an operation section 3 disposed on a proximal end side of the insertion section 2; and a universal cord 4 extending from the operation section 3.

A bending operation apparatus 11, an air/water feeding button 12, a suction button 13, a raising base operation lever 14, and operation switches 15 are provided on the operation section 3.

The operation switches 15 are formed of a freeze switch which generates a freeze signal, a release switch which generates a release signal for taking a picture, an observation mode switching switch for instructing switching of an observation mode and the like.

A treatment instrument insertion opening 16 through which a treatment instrument (not shown) is introduced into a body is formed in the operation section 3. One end side of a channel tube 17 is connected to the treatment instrument insertion opening 16. The other end side of the channel tube 17 is connected to a distal end member 20 which forms a distal end portion 5 of the insertion section 2.

The insertion section 2 is formed of the distal end portion 5, a bending portion 6, and a flexible tube portion 7 which are disposed in this order from a distal end side. The distal end cover 30 is mounted on the distal end portion 5. The detail of the configurations of the distal end portion 5 and the distal end cover 30 is described later.

The flexible tube portion 7 is formed of, for example, a helical tube, a meshed tube which covers the helical tube, and a heat shrinking tube which forms an outermost layer, all of which are not shown.

The bending portion 6 is formed of: a set of bending pieces configured to bend in four directions, for example, upward, downward, leftward and rightward directions; a metal made meshed tube which covers the set of bending pieces; and a bending rubber which forms an outer skin. The bending portion 6 bends in the upward direction or in the downward direction by rotatably operating an upward and downward bending knob 11a, and bends in the leftward direction or in the rightward direction by rotatably operating a leftward and rightward bending knob 11b, of the bending operation apparatus 11 provided on the operation section 3.

Figure 2:
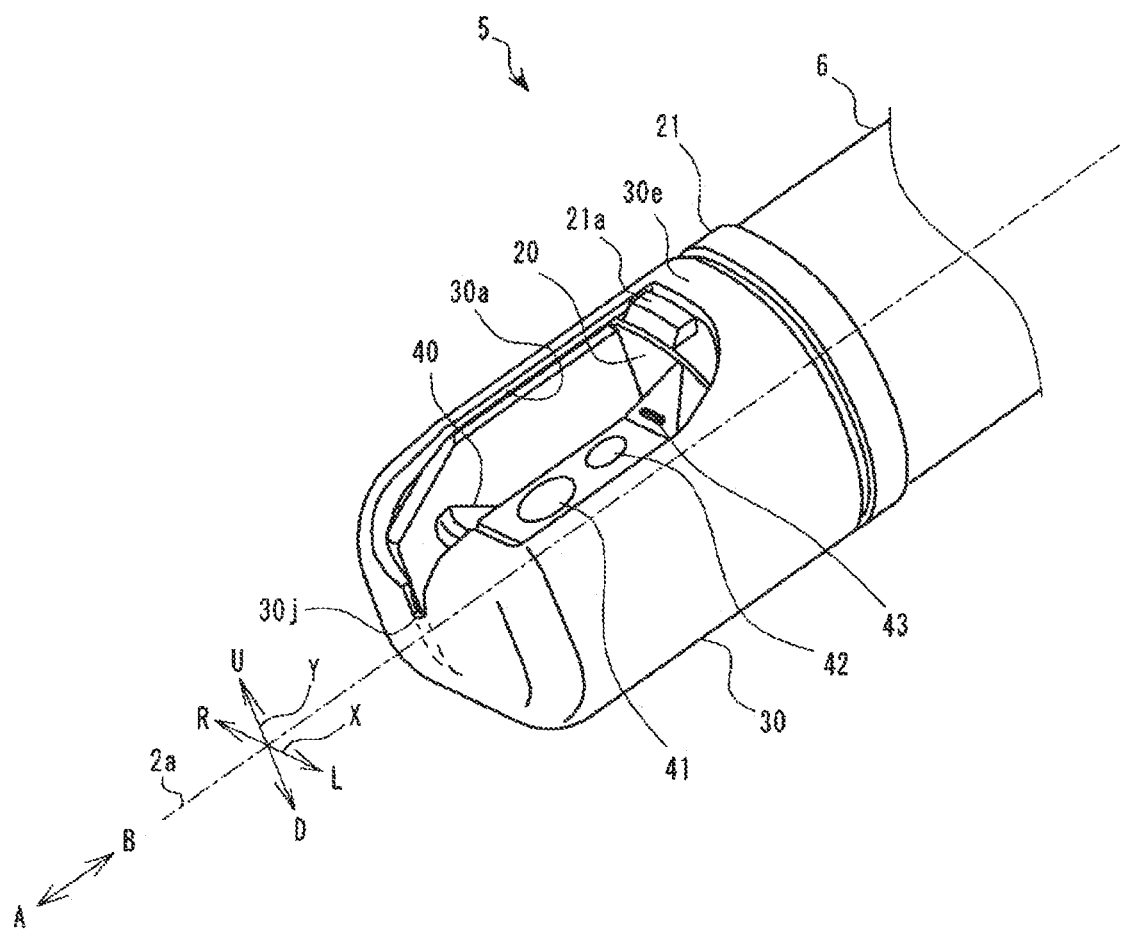
FIG. 2 is a perspective view of a distal end portion of an insertion section.

FIG. 2 is a perspective view of the distal end portion 5. As shown in FIG. 2, the distal end cover 30 is mounted on the distal end portion 5. The distal end cover 30 is a sheath-like member which covers a predetermined outer surface of the distal end portion 5, and is detachably mounted on the distal end portion 5.

Figure 3:
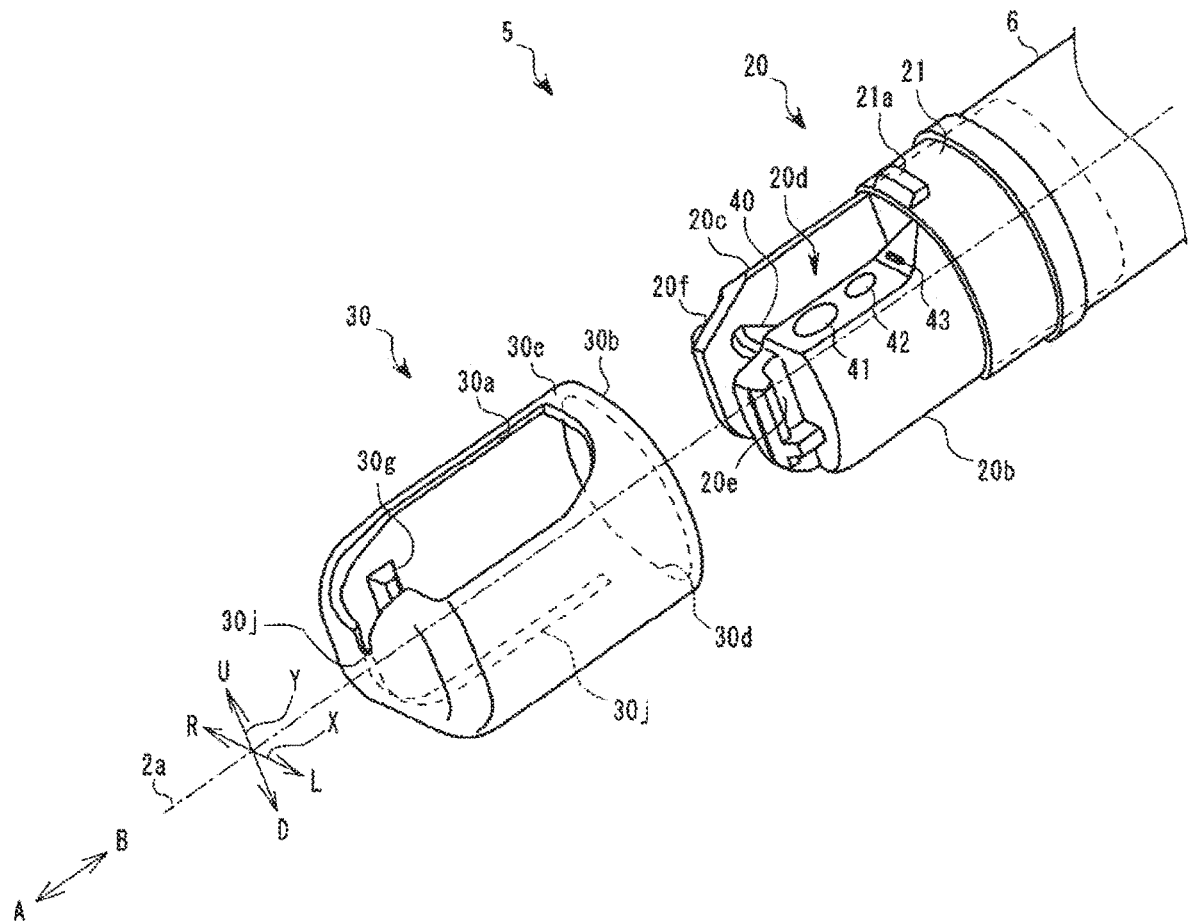
FIG. 3 is a perspective view showing a state where a distal end cover and the distal end portion are separated from each other.

The distal end cover 30 includes a to-be-torn-apart portion 30j which is a portion where a torn-apart which is irreversible deformation occurs when the distal end cover 30 is removed from the distal end portion 5 after the distal end cover 30 is mounted on the distal end portion 5 once. FIG. 3 is a perspective view showing a state where the distal end cover 30 and the distal end portion 5 are separated from each other. FIG. 3 shows the distal end cover 30 in a state where the distal end cover 30 has never been mounted on the distal end portion 5 (unused state).

The distal end cover 30 is made of a resin having an electrical insulation property, and has predetermined elasticity. A kind of the resin which forms the distal end cover 30 is not particularly limited. However, in the embodiment, as one example, the distal end cover 30 is formed of a resin which has low elasticity compared to rubber or the like, and is easily plastically deformed and torn apart among resins such as polyethylene or polypropylene. By forming the distal end cover 30 using such a resin, it is possible to easily generate irreversible deformation or breaking (torn-apart) in the distal end cover 30 when the distal end cover 30 is removed from the distal end portion 5. By generating irreversible deformation or breaking (torn-apart) in the distal end cover 30 removed from the distal end portion 5, it is possible to prevent the reuse of the distal end cover 30.

The distal end cover 30 is preferably made of a semi-transparent or transparent resin. By forming the distal end cover 30 using a semitransparent or transparent resin, a user of the endoscope 1 can easily visually recognize whether or not the distal end cover 30 is accurately mounted on the distal end member 20 at a predetermined position.

In the description made hereinafter, an axis extending along a longitudinal direction of the elongated insertion section 2 is referred to as a longitudinal axis 2a. A direction extending toward the distal end side of the insertion section 2 along the longitudinal axis 2a is referred to as a distal end direction A, and a direction opposite to the distal end direction A is referred to as a proximal end direction B. Two straight line axes which are orthogonal to each other on a plane which is orthogonal to the longitudinal axis 2a are defined as an X axis and a Y axis. A direction extending toward one side along the X axis is referred to as a right direction R, and a direction opposite to the right direction R is referred to as a left direction L. A direction extending toward one side along the Y axis is referred to as an upward direction U, and a direction opposite to the upward direction U is referred to as a downward direction D. The X axis and the Y axis are substantially parallel to the bending direction of the bending portion 6.

In the embodiment, as one example, assume that a right side is the right direction R and an upper side is the upward direction in a case where the distal end portion 5 is viewed from a proximal end side to a distal end side along the longitudinal axis 2a and the X axis is disposed horizontally.

As shown in FIG. 3, the distal end portion 5 includes the distal end member 20 made of metal, and an insulation portion 21 made of a resin or ceramic having an electrical insulation property.

The distal end member 20 includes: a proximal portion 20a which is fixed to a distal end of the bending portion 6; a first arm portion 20b and a second arm portion 20c which are a pair of arm portions protruding toward the distal end direction A from the proximal portion 20a; and a raising base accommodating space 20d which is a space formed between the first arm portion 20b and the second arm portion 20c. A raising base (forceps elevator) 40 is rotatably disposed in the raising base accommodating space 20d.

An illumination lens 41, an observation lens (imaging lens) 42, and a cleaning nozzle 43 are disposed on an upper surface of an outer peripheral surface of the first arm portion 22 facing in the upward direction U. The observation lens 42 is provided for picking up an image of an object, and the illumination lens 41 is provided for irradiating an illumination light toward the object. The center of a field of view of the observation lens 42 extends substantially in the upward direction U. In other words, a side of the insertion section 2 falls within the field of view of the observation lens 42. The cleaning nozzle 43 is a part which ejects a fluid toward the illumination lens 41 and the observation lens 42.

The raising base 40 is disposed in the raising base accommodating space 24 in a state where the raising base 40 is rotatable about a rotation axis substantially parallel to the X axis. A rotation operation of the raising base 40 is performed by the raising base operation lever 14 provided on the operation section 3. A mechanism such as a wire for transmitting the movement of the raising base operation lever 14 to the raising base 40 is disposed in the second arm portion 20c.

Engaging grooves 20e and 20f are formed by carving in a recessed manner in the vicinity of a distal end of the first arm portion 20b and in the vicinity of a distal end of the second arm portion 20c. The engaging groove 20e has a concave shape extending from a left side surface of the first arm portion 20b to the inside (rightward direction R). The engaging groove 20f has a concave shape extending from a right side surface of the second arm portion 20c toward the inside (leftward direction L). The engaging grooves 20e and 20f formed on an outer surface of the distal end member 20 are parts which engage with a pair of locking pawls 30g (described later) which are formed on an inner surface of the distal end cover 30.

As described previously, the insulation portion 21 is made of a resin or ceramic having an electrical insulation property. The insulation portion 21 is a ring-shaped member which covers an outer periphery of the proximal portion 20a of the distal end member 20. The proximal portion 20a has a columnar shape along the longitudinal axis 2a. The insulation portion 21 is formed in a ring shape about the longitudinal axis 2a, and covers the outer peripheral surface of the proximal portion 20a over the entire circumferential direction.

A locking pawl 21a which protrudes toward the upward direction U is formed on an upper surface of the outer peripheral surface of the insulation portion 21 facing the upward direction U. The locking pawl 21a is a part which engages with an annular portion 30e (described later) of the distal end cover 30.

Figure 4:
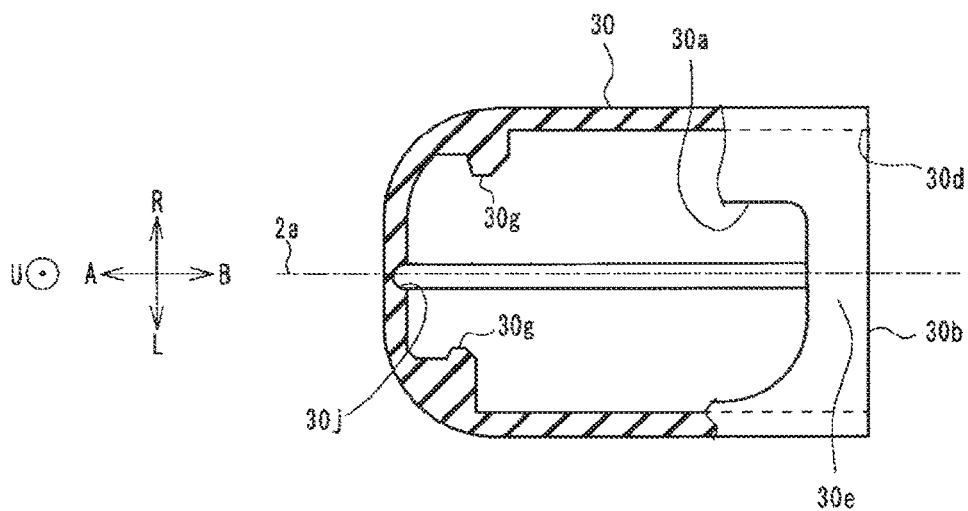
FIG. 4 is a partial cross sectional view of the distal end cover as viewed from an upward direction toward a downward direction.

Next, the configuration of the distal end cover 30 described above is described. FIG. 4 is a partial cross-sectional view of the distal end cover 30 as viewed from the upward direction U toward the downward direction D.

The distal end cover 30 is a sheath-like member where a distal end direction A side is closed and a proximal end direction B side opens.

An opening formed in the proximal end direction B side of the distal end cover 30 is referred to as an insertion opening 30d. In mounting the distal end cover 30 on the distal end portion 5, the distal end portion 5 is inserted into the distal end cover 30 through the insertion opening 30d.

The distal end cover 30 has an opening portion 30a through which the raising base accommodating space 20d is exposed only toward the upward direction U in a state where the distal end cover 30 is mounted on the distal end portion 5. The illumination lens 41, the observation lens 42, and the cleaning nozzle 43 are also exposed toward the upward direction U through the opening portion 30a in a state where the distal end cover 30 is mounted on the distal end member 20.

The opening portion 30a is not connected with the insertion opening 30d on the outer surface of the distal end cover 30. Accordingly, the annular portion 30e which is connected in an annular shape over the entire circumference around the longitudinal axis 2a is formed on a proximal end 30b of the distal end cover 30.

In a state where the distal end cover 30 is mounted on the distal end member 20, the annular portion 30e is brought into close contact with an outer peripheral surface of the insulation portion 21 on the proximal end direction B side with respect to the locking pawl 21a formed on the insulation portion 21. Further, in such a state, the locking pawl 21a protrudes into the opening portion 30a. In other words, in a state where the distal end cover 30 is mounted on the distal end portion 5, the locking pawl 21a engages with the annular portion 30e thus restricting the movement of the distal end cover 30 relative to the distal end portion 5 in the distal end direction A.

The pair of locking pawls 30g and the to-be-torn-apart portion 30j are formed on the distal end cover 30. The pair of locking pawls 30g are convex-shaped parts which project toward the inside from an inner peripheral surface of the distal end cover 30. In a state where the distal end cover 30 is mounted on the distal end portion 5, the pair of locking pawls 30g are fitted in the engaging grooves 20e and 20f of the distal end member 20.

By engagement of the pair of locking pawls 30g with the engaging grooves 20e and 20f, in a state where the distal end cover 30 is mounted on the distal end member 20, the movement of the distal end cover 30 relative to the distal end member 20 in the distal end direction A is restricted.

The to-be-torn-apart portion 30j includes: a cutout formed by cutting out a portion of a peripheral portion of the opening portion 30a in a V shape or a U shape; and a groove extending along an inner peripheral surface of the distal end cover 30 from the cutout. The to-be-torn-apart portion 30j is disposed between the pair of locking pawls 30g. An end portion of the to-be-torn-apart portion 30j on the proximal end direction B side extends to substantially the same position as an end portion of the opening portion 30a on the proximal end direction B side. In other words, the to-be-torn-apart portion 30j is not formed on an inner peripheral surface 30f of the annular portion 30e of the distal end cover 30. Accordingly, close contact property between the inner peripheral surface 30f of the annular portion 30e and the insulation portion 21 is further enhanced.

When an external force which tears the to-be-torn-apart portion 30j of the distal end cover 30 is applied to the distal end cover 30 by a finger of a user, for example, the to-be-torn-apart portion 30j is torn apart. When the to-be-torn-apart portion 30j is torn apart in a state where the distal end cover 30 is mounted on the distal end portion 5, a spaced-apart distance between the pair of locking pawls 30g is increased and hence, mounting of the distal end cover 30 on the distal end portion 5 is released. Further, even when a user intends to mount the distal end cover 30 where the to-be-torn-apart portion 30j is torn apart on the distal end portion 5, the pair of locking pawls 30g are not fitted in the engaging grooves 20e and 20f and hence, it is impossible to fix the distal end cover 30 to the distal end portion.

Figure 5:
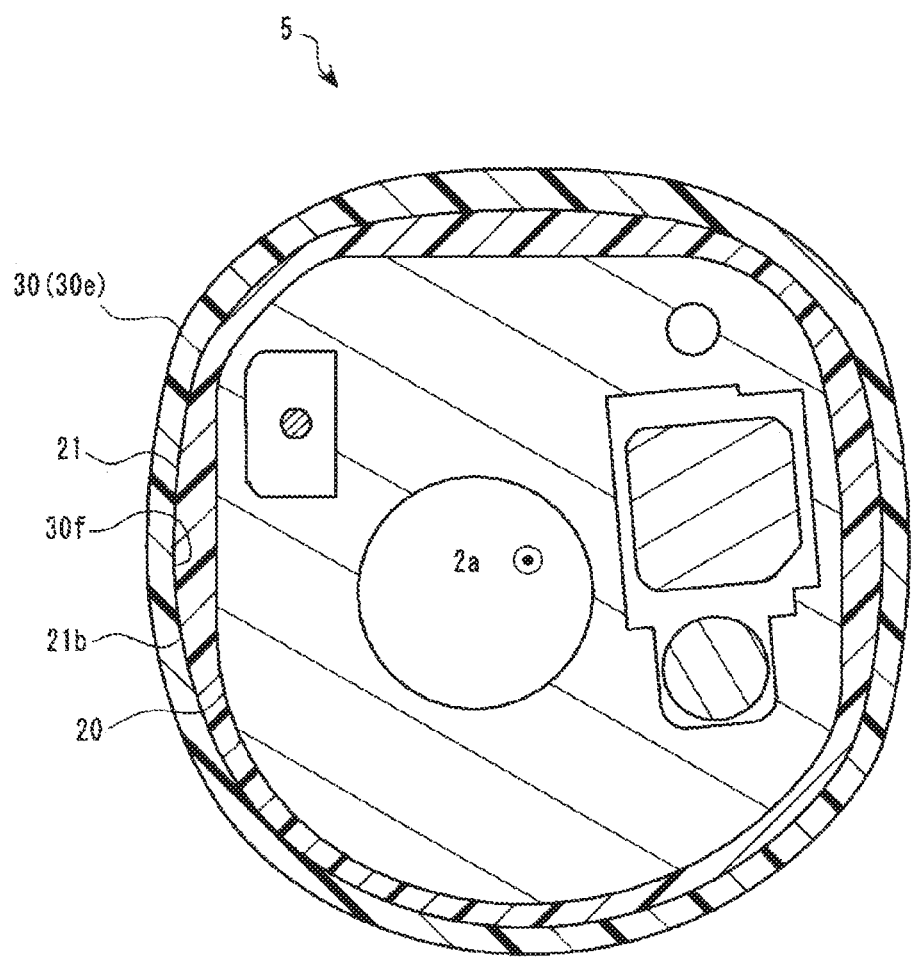
FIG. 5 is a cross-sectional view of a part of the distal end portion where an insulation portion is formed taken along a plane orthogonal to an insertion axis.
Figure 5:
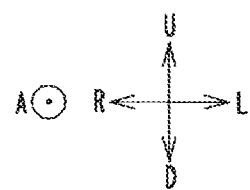

FIG. 5 is a cross-sectional view of the distal end portion 5 at the insulation portion 21 taken along a plane orthogonal to the longitudinal axis 2a. FIG. 5 shows a state where the distal end cover 30 is mounted on the distal end portion 5.

As described previously, in a state where the distal end cover 30 is mounted on the distal end portion 5, the inner peripheral surface 30f of the annular portion 30e of the distal end cover 30 is brought into close contact with the outer peripheral surface of the insulation portion 21 of the distal end portion 5. Accordingly, a cross-sectional shape of an outer peripheral surface 21b of the insulation portion 21 taken along a plane orthogonal to the longitudinal axis 2a is similar to a cross-sectional shape of the inner peripheral surface 30f of the annular portion 30e taken along the plane orthogonal to the longitudinal axis 2a. Further, in a state where the distal end cover 30 is not mounted on the distal end portion 5, an inner peripheral shape of the inner peripheral surface 30f of the annular portion 30e is slightly smaller than an outer peripheral shape of the outer peripheral surface 21b of the insulation portion 21. The annular portion 30e and the insulation portion 21 have a so-called close fit relationship.

In the embodiment, the outer peripheral surface 21b of the insulation portion 21 and the inner peripheral surface 30f of the annular portion 30e do not have a simple cylindrical shape, and have a shape formed by connecting a plurality of curved surfaces having different curvatures around the longitudinal axis 2a.

As shown in FIG. 5, in the embodiment, the outer peripheral surface 21b of the insulation portion 21 is formed of curved surfaces which are convex toward the outside in a radial direction over the entire circumference around the longitudinal axis 2a. Further, all curved surfaces respectively having the plurality of curvatures which form the outer peripheral surface 21b of the insulation portion 21 are smoothly connected to each other.

In other words, the cross-sectional shape of the outer peripheral surface 21b taken along a plane orthogonal to the longitudinal axis 2a becomes a closed curve having curvatures which are convex toward the outside in the radial direction over the entire circumference around the longitudinal axis 2a and having neither straight lines nor inflection points. Further, the closed curve is formed by connecting a plurality of curves having different curvatures. However, at a connecting portion between the curves disposed adjacently to each other, tangents of both curves agree with each other so that both curves are smoothly connected to each other without bending.

In the same manner, the inner peripheral surface 30f of the annular portion 30e of the distal end cover 30 is formed of curved surfaces which are concave toward the outside in the radial direction over the entire circumference around the longitudinal axis 2a. Further, all curved surfaces respectively having the plurality of curvatures which form the inner peripheral surface 30f of the annular portion 30e are smoothly connected to each other.

In other words, the cross-sectional shape of the inner peripheral surface 30f taken along a plane orthogonal to the longitudinal axis 2a becomes a closed curve having curvatures which are convex toward the outside in the radial direction over the entire circumference around the longitudinal axis 2a and having neither straight lines nor inflection points. Further, the closed curve is formed by connecting a plurality of curves having different curvatures. However, at a connecting portion between the curves disposed adjacently to each other, tangents of both curves agree with each other so that both curves are smoothly connected to each other without bending.

In the endoscope system 100 of the embodiment having the above-mentioned configuration, the outer peripheral surface 21b of the insulation portion 21 is formed of the smooth curved surfaces which are convex toward the outside in the radial direction over the entire circumference. Accordingly, it is possible to bring the annular portion 30e of the distal end cover 30 which covers the outer peripheral surface 21b into close contact with the outer peripheral surface 21b without gap over the entire circumference.

To describe more specifically, for example, in the case where flat surfaces or concave surfaces exist on the outer peripheral surface of the insulation portion, even when the outer peripheral surface of the insulation portion and the inner peripheral surface of the annular portion have similar shapes, a force which presses the inner peripheral surface of the annular portion to the flat surfaces and the concave surfaces of the insulation portion becomes weak and hence, a liquid is liable to intrude between the insulation portion and the annular portion. Particularly, in the case where the distal end cover (annular portion) is made of a resin having low elasticity and is liable to cause plastic deformation or a torn-apart compared to rubber or the like, it is difficult to bring the annular portion into close contact with and along the flat surfaces and the concave surfaces of the insulation portion by elastic deformation of the annular portion thus giving rise to a possibility that a gap is formed between the insulation portion and the annular portion. Further, also in the case where a connecting portion between curved surfaces having different curvatures is bent on the outer peripheral surface of the insulation portion, it is difficult to deform the annular portion in conformity with such bending thus giving rise to a possibility that a gap is formed between the insulation portion and the annular portion.

On the other hand, in the embodiment, neither the flat surfaces nor the concave surfaces exist on the outer peripheral surface 21b of the insulation portion 21, and no bending exists on the outer peripheral surface 21b of the insulation portion 21. Accordingly, in the case where the insulation portion 21 is fitted in the annular portion 30e, a force which presses the entire circumference of the inner peripheral surface 30f of the annular portion 30e to the outer peripheral surface 21b of the insulation portion 21 is generated.

With such a configuration, according to the embodiment, although the distal end cover 30 is made of a resin having low elasticity compared to rubber or the like and being easily plastically deformed or torn apart among resins such as polyethylene or polypropylene, the annular portion 30e can be deformed in conformity with the shape of the insulation portion 21 and can be brought into close contact with the insulation portion 21 by pressing the annular portion 30e to the insulation portion 21 over the entire circumference around the longitudinal axis 2a.

Accordingly, in the endoscope system 100 of the embodiment, it is possible to prevent the intrusion of a liquid between the insulation portion 21 and the distal end cover 30 and hence, it is possible to prevent leaking of a high frequency current at the time of performing high frequency cauterization.

The present invention is not limited to the embodiment described above, and can be suitably modified without departing from the gist or the concept of the present invention read from claims and the entire specification. Endoscope systems which adopt such modification also fall within the technical scope of the present invention.

What is claimed is:

1. An endoscope system comprising:

an endoscope including an insertion section extending in a longitudinal axis direction, a distal end member disposed on a distal end portion of the insertion section, and a ring-shaped insulation member disposed on a proximal end side of the distal end member and about the longitudinal axis; and a distal end cover mounted on the distal end portion of the insertion section, the distal end cover including an opening configured to expose a portion of the distal end member, the distal end cover further including an inner peripheral surface disposed on a proximal end side with respect to the opening, the inner peripheral surface being brought into close contact with an outer peripheral surface of the insulation member, wherein in a cross-section perpendicular to the longitudinal axis, the outer peripheral surface of the insulation member is a first shape consisting of a plurality of convex curved surfaces each having a different curvature from each other; and in the cross-section perpendicular to the longitudinal axis, the inner peripheral surface of the distal end cover having a second shape consisting of a plurality of concave curved surfaces each having a different curvature from each other.

2. The endoscope system according to claim 1, wherein the distal end cover is formed of a resin which has a low elasticity and is easily plastically deformed and broken.

3. The endoscope system according to claim 1, wherein a surface of the distal end member extending along the longitudinal axis is exposed through the opening of the distal end cover.

4. The endoscope system according to claim 1, wherein the distal end member has conductivity.

5. The endoscope system according to claim 1, wherein mounting of the distal end cover on the distal end portion is released by breaking of the distal end cover with an external force.

6. The endoscope system according to claim 1, wherein the distal end member includes an imaging unit for observing a direction which intersects with the longitudinal axis through the opening of the distal end cover.

7. The endoscope according to claim 1, wherein an elasticity of the distal end cover is lower than an elasticity of a rubber.

8. An endoscope comprising:
a distal end member disposed on a distal end of an insertion section which extends along a longitudinal axis, wherein a cover is mounted on the distal end member; and
a ring-shaped insulation member disposed on a proximal end side of the distal end member and about the longitudinal axis, wherein
an outer peripheral surface of the insulation member configured to be brought into close contact with an inner peripheral surface of the cover, in a cross-section perpendicular to the longitudinal axis, the outer peripheral surface is a shape consisting of a plurality of convex curved surfaces each having a different curvature from each other.

9. The endoscope according to claim 8, wherein the distal end member has conductivity.

10. The endoscope according to claim 8, wherein the distal end member includes an imaging unit for observing a direction which intersects with the longitudinal axis.

* * * * *